United States Patent
Beard et al.

(10) Patent No.: US 6,177,588 B1
(45) Date of Patent: *Jan. 23, 2001

(54) 1-ALKOXY AND 1-ACYLOXY SUBSTITUTED CYCLOHEX-1-ENE COMPOUNDS AND SULFUR AND 1-ALKOXYCARBONYL ANALOGS HAVING RETINOID-LIKE BIOLOGICAL ACTIVITY

(75) Inventors: Richard L. Beard; Diana F. Colon, both of Newport Beach; Roshantha A. Chandraratna, Mission Viejo, all of CA (US)

(73) Assignee: Allergan Sales, Inc., Irvine, CA (US)

( * ) Notice: Under 35 U.S.C. 154(b), the term of this patent shall be extended for 0 days.

This patent is subject to a terminal disclaimer.

(21) Appl. No.: 09/307,073

(22) Filed: May 7, 1999

(51) Int. Cl.$^7$ .......................... C07C 69/76; C07C 309/01
(52) U.S. Cl. ................... 560/76; 560/81; 558/52; 556/437; 556/440
(58) Field of Search .................. 560/76, 81; 558/52; 556/437, 440

(56) References Cited

U.S. PATENT DOCUMENTS

| | | |
|---|---|---|
| 4,391,731 | 7/1983 | Boller et al. . |
| 4,539,154 | 9/1985 | Krebs . |
| 4,739,098 | 4/1988 | Chandraratna . |
| 4,923,884 | 5/1990 | Chandraratna . |
| 4,927,947 | 5/1990 | Chandraratna . |
| 5,426,118 | 6/1995 | Chandraratna et al. . |
| 5,451,605 | 9/1995 | Chandraratna et al. . |
| 5,455,265 | 10/1995 | Chandraratna . |
| 5,470,999 | 11/1995 | Chandraratna . |
| 5,618,836 | 4/1997 | Chandraratna et al. . |
| 5,760,276 | 6/1998 | Beard et al. . |
| 5,877,207 | 3/1999 | Klein et al. . |

FOREIGN PATENT DOCUMENTS

| | | |
|---|---|---|
| 0272921 | 6/1988 | (EP) . |
| 93/11755 | 6/1993 | (WO) . |

OTHER PUBLICATIONS

Dawson and William H. Okamura, *Chemistry and Biology of Synthetic Retinoids* published by CRC Press, Inc., 1990, pp. 334–335.

Negishi et al., "Conversion of Methyl Ketones into Terminal Acetylenes and (E)–Trisubstituted Olefins of Terpenoid Origin", *J. Org. Chem.* 45 No. 12, 1980 p. 2526.
Verma & Boutwell, Cancer Research, (1977), 37 2196–2201.
Cancer Research: 1662–1670 (1975).
Feigner P. L. and Holm M. (1989) Focus, 112.
Heyman et al., Cell 68, 397–406, (1992).
Allegretto et al., J. Biol. Chem. 268, 26625–26633.
Mangelsdorf et al., The Retinoids: Biology, Chemistry and Medicine, pp. 319–349, Raven Press Ltd., New York.
Cheng et al., Biochemical Pharmacology vol. 22 pp. 3099–3108.
Klein et al., J. Biol. Chem. 271, 22692–22696 (1996).
Chen et al. (1987) Mol. Cell. Biol. 7, 2745–2752.
de Wet (1987) Mol. Cell. Biol. 7, 725–737.
Nagpal et al., EMBO J. 12, 2349–2360 (1993).
Corey, E. J., Schmidt, G., *Tet. Lett.*, 399, (1979).
Omura, K., Swern D., *Tetrahedron*, 1978, 34, 1651.

*Primary Examiner*—Gary Geist
*Assistant Examiner*—Leigh C. Maier
(74) *Attorney, Agent, or Firm*—Gabor L. Szekeres; Robert J. Baran; Martin A. Voet

(57) ABSTRACT

Compounds of Formula 1 and of Formula 2

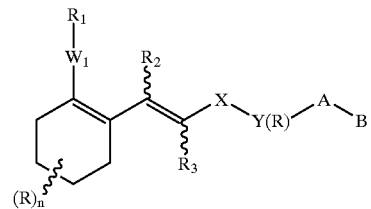

Formula 1

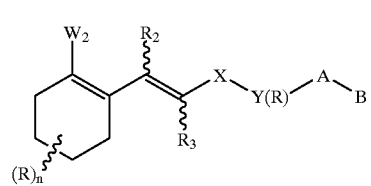

Formula 2 where the symbols have the meaning defined in the specification, have retinoid, retinoid antagonist or retinoid negative hormone like biological activity.

22 Claims, No Drawings

1-ALKOXY AND 1-ACYLOXY SUBSTITUTED CYCLOHEX-1-ENE COMPOUNDS AND SULFUR AND 1-ALKOXYCARBONYL ANALOGS HAVING RETINOID-LIKE BIOLOGICAL ACTIVITY

BACKGROUND OF THE INVENTION

1. Field of the Invention

The present invention relates to novel compounds having retinoid-like biological activity. More specifically, the present invention relates to 1-alkoxy and 1-acyloxycyclohex-1-enyl and aryl or 1-alkoxy and 1-acyloxycyclohex-1-enyl and heteroaryl substituted alkene derivatives and to their sulfur and 1-alkoxycarbonyl analogs having retinoid-like, retinoid antagonist or retinoid inverse agonist-like biological activity.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

Although pharmaceutical compositions containing retinoids have well established utility, retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist) or the compound may elicit an agonist-like response on all receptor subtypes (pan-agonist). As still another alternative a compound may be a partial agonist and/or partial antagonist of certain receptor subtypes if the compound binds to but does not activate certain receptor subtype or subtypes but elicits an agonist-like response in other receptor subtype or subtypes. A pan-antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists. U.S. Pat. No. 5,877,207 titled "Synthesis and Use of Retinoid Compounds Having Negative Hormone and/or Antagonist Activities" describes the foregoing two-state model and the use of retinoid antagonist and negative hormones in detail.

Inasmuch as naturally occurring retinoic acid includes a cyclohexene moiety, numerous patents and scientific publications which relate to the chemistry and biology of retinoids and related compounds are of interest as background to the present invention. Among the scientific publications Dawson and William H. Okamura, *Chemistry and Biology of Synthetic Retinoids* published by CRC Press Inc., 1990, pages 334–335, 354 and 324–356 is of special interest as an overview of the prior art on the subject. The publication Negishi, Ei-ichi, Anthony O. King, and William L. Klima, "Conversion of Methyl Ketones into Terminal Acetylenes and (E)-Trisubstituted Olefins of Terpenoid Origin", *J. Org. Chem.* 45 No. 12, 1980 p. 2526 is of interest as it relates to a process of synthesizing certain cyclohexene derivatives.

Among the numerous United States and foreign patents which disclose compounds having retinoid agonist, antagonist or inverse agonist like biological activity and are known to applicant, the following include a cyclohexane or cyclohexene ring structure and therefore are of interest as background to the present invention: U.S. Pat. Nos. 5,760,276; 5,618,836; 5,470,999; 5,451,605; 5,426,118; 4,539,154; 4,739,098; 4,923,884; 4,927,947 and EPO 0 272 921. U.S. Pat. No. 4,391,731; discloses certain cyclohexane derivatives suitable for use as liquid crystals.

SUMMARY OF THE INVENTION

The present invention relates to compounds of Formula 1 and Formula 2

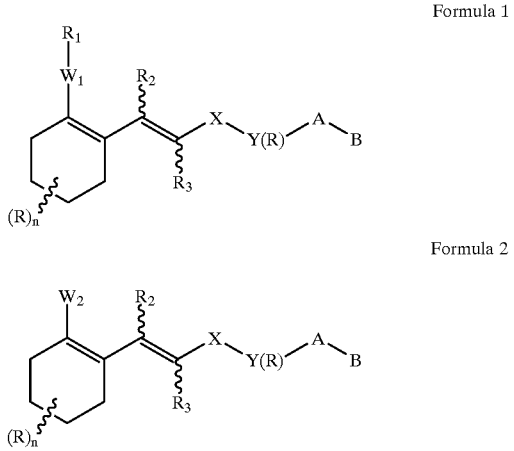

Formula 1

Formula 2 where $R_1$ is alkyl of 1 to 10 carbons, $(R_4)_p$-phenyl, $(R_4)_p$-heteroaryl, RCO, RCS, trifluoromethylsulfonyl, or $C_1$–$C_6$ trialkylsilyl;

$W_1$ of Formula 1 is O or S;

$W_2$ of Formula 2 is $CH_2OR_2$, $R_2CO$, $CO_2R_2$ COSR, $CON(R_2)_2$ or CN;

p is an integer having the values 0 to 5;

R is H, lower alkyl of 1 to 10 carbons, cycloalkyl of 3 to 10 carbons, halogen, $(C_{1-10}$-lower alkyl$)_3$-silyl, $C_{1-10}$-lower alkylphenyl, or phenyl-$C_{1-10}$-lower alkyl;

$R_2$ and $R_3$ are lower alkyl of 1 to 10 carbons, cycloalkyl of 3 to 10 carbons, $(C_{1-10}$-lower alkyl$)_3$-silyl, $C_{1-10}$-lower alkylphenyl, or phenyl-$C_{1-10}$-lower alkyl;

$R_4$ is alkyl of 1 to 10 carbons, F, Cl, Br, I, $NO_2$, $N_3$, $(CH_2)_p COOH$, $(CH_2)_p COOR$;

n is an integer having the values of 0 to 6;

X is C≡C, C(O)O, C(O)S, CONR, CSNR, and $(CR=CR)_{n'}$, where n' is an integer having the values 1 to 5;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R groups, or when X is —$(CR=CR)_{n'}$— and n' is 3, 4 or 5 then Y represents a direct valence bond between said $(CR=CR)_{n'}$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound.

In a second aspect, this invention relates to the use of the compounds of Formula 1 and 2 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds are also useful for the prevention and treatment of metabolic diseases such as type II diabetes and diabetes mellitus and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreo-retinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

Alternatively, those compounds of the invention which act as antagonists or inverse agonists of one or more retinoid receptor subtypes are useful to prevent certain undesired side effects of retinoids which are administered for the treatment or prevention of certain diseases or conditions. For this purpose the retinoid antagonist and/or inverse agonist compounds of the invention may be co-administered with retinoids. The retinoid antagonist and inverse agonist compounds of the present invention are also useful in the treatment of acute or chronic toxicity resulting from overdose or poisoning by retinoid drugs or Vitamin A.

This invention also relates to a pharmaceutical formulation comprising a compound of Formula 1 or 2 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

BIOLOGICAL ACTIVITY, MODES OF ADMINISTRATION

Assays of Retinoid-like or Retinoid Antagonist and Inverse Agonist-like Biological Activity A classic measure of retinoic acid activity involves measuring the effects of retinoic acid on ornithine decarboxylase (ODC). The original work on the correlation between retinoic acid and decrease in cell proliferation was done by Verma & Boutwell, Cancer Research, 1977, 37, 2196–2201. That reference discloses that ornithine decarboxylase activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. "$IC_{60}$" is that concentration of the test compound which causes 60% inhibition in the ODC assay. By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$ and $RXR_\gamma$ receptors, and the ability or inability of the compounds to activate transcription of a reporter gene through these receptor subtypes can be tested. These assays are expected to demonstrate that the compounds of the present invention act as agonists of one or more of the above-described receptors. However, some of the compounds of the invention may behave as retinoid antagonists or partial antagonists and/or as inverse agonists. Because of the complex distribution of the different retinoid receptors in various organs of the mammalian body partial agonists and partial antagonists and compounds which have the characteristics of both may lend themselves to particularly useful therapeutic applications and may avoid serious side effects of conventional retinoid drugs.

As far as specific assays are concerned to demonstrate the activities of the compounds of the present invention, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO W093/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et al. Biochemical Pharmacology Vol. 22 pp 3099–3108, expressly incorporated herein by reference.) Still another transactivation assay, the "PGR assay" is described in the publication Klein et al. J. Biol. Chem. 271, 22692–22696 (1996) which is expressly incorporated herein by reference, and a detailed description is also provided below. The results of the PGR assay are also expressed in $EC_{50}$ numbers (nanomolar concentration).

RAR-P-GR holoreceptor Transactivation Assay

CV-1 cells ($4 \times 10^5$ cells/well) were transiently transfected with the luciferase reporter plasmid MTV-4(R5G)-Luc (0.7 ug/well) containing four copies of the R5G retinoid DNA response element along with the $RXR_\alpha$ expression plasmid pRS-hRXRα (0.1 ug/well) and one of the RAR-P-GR expression plasmids (0.05 ug/well) in 12 well plates via calcium phosphate precipitation Chen et al. (1987) Mol. Cell. Biol. 7, 2745–2752 as described by Klein et al. in J. Biol. Chem. 271, 22692, referenced above. The three different RAR-P-GR expression plasmids, pRS-RARα-P-GR, pcDNA3-RARβ-P-GR and pcDNA3-RARγ-P-GR, express RARα, RARβ and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except ⅕ of the amount of the DNA-calcium phosphate precipitant (20 μl instead of 100 μl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed with luciferase activity was measured as previously described in de Wet (1987) Mol. Cell. Biol. 7, 725–737. Luciferase values represent the mean±SEM of triplicate determinations normalized to β-galactosidase activity.

Inverse agonists are ligands that are capable of inhibiting the basal receptor activity of unliganded receptors. Recently, retinoic acid receptors (RARs) have been shown to be responsive to retinoid inverse agonists in regulating basal gene transcriptional activity. Moreover, the biological effects associated with retinoid inverse agonists are distinct from those of retinoid agonists or antagonists. For example, RAR inverse agonists, but not RAR neutral antagonists, cause a dose-dependent inhibition of the protein MRP-8 in cultured human keratinocytes differentiated with serum. MRP-8 is a specific marker of cell differentiation, which is also highly expressed in psoriatic epidermis, but is not detectable in normal human skin. Thus, retinoid inverse agonists may offer a unique way of treating diseases such as psoriasis.

The activity of retinoid inverse agonists can be tested by the procedure of Klein et al. *J. Biol. Chem.* 271, 22692–22696 (1996) which is expressly incorporated herein by reference. In this assay, retinoid inverse agonists are able to repress the basal activity of a RARγ-VP-16 chimeric receptor where the constituitively active domain of the herpes simplex virus (HSV) VP-16 is fused to the N-terminus of RARγ. CV-1 cells are cotransfected with RARγ-VP-1 6, an ER-RXRα chimeric receptor and an ERE-tk-Luc chimeric reporter gene to produce a basal level of luciferase activity, as shown by Nagpal et al. *EMBO J.* 12, 2349–2360 (1993) expressly incorporated herein by reference. Retinoid inverse agonists are able to inhibit the basal luciferase activity in these cells in a dose dependent manner and $IC_{50}s$ measured. A detailed description of the tests used for determining whether or not a compound is a retinoid antagonist or inverse agonist, and the manner of utilizing retinoid antagonists and inverse agonists is provided in U.S. Pat. No. 5,877,207, the specification of which is expressly incorporated herein by reference.

Table 1 discloses the activity of certain exemplary compounds of the invention in the above-described ornithine decarboxylase (ODC) assay.

TABLE 1

| Ornithine Decarboxylase (ODC) assay | |
|---|---|
| Compound # | $IC_{60}$ $IC_{80}$ (nanomolar) |
| 1 | 0.46[1] |
| 6 | 0.3[2] |

[1]$IC_{80}$
[2]$IC_{60}$

Modes of Administration

The compounds of this invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

The partial or pan retinoid antagonist and/or retinoid inverse agonist compounds of the invention, when used to take advantage of their antagonist and/or inverse agonist property, can be co-administered to mammals, including humans, with retinoid agonists and, by means of pharmacological selectivity or site-specific delivery, preferentially prevent the undesired effects of certain retinoid agonists. The antagonist and/or inverse agonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist and/or inverse agonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist or inverse agonist compounds of the present invention block or diminish RAR activation, they are suitable for treating the foregoing toxicities.

Generally speaking, for therapeutic applications in mammals, the antagonist and/or inverse agonist compounds of the invention can be admistered enterally or topically as an antidote to vitamin A, or antidote to retinoid toxicity resulting from overdose or prolonged exposure, after intake of the causative factor (vitamin A, vitamin A precursor, or other retinoid) has been discontinued. Alternatively, the antagonist and/or inverse agonist compounds of the invention are co-administered with retinoid drugs, in situations where the retinoid provides a therapeutic benefit, and where the co-administered antagonist and/or inverse agonist compound alleviates or eliminates one or more undesired side effects of the retinoid. For this type of application the antagonist and/or inverse agonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For topical application, the antagonist and/or inverse agonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

The antagonist and/or inverse agonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist and/or inverse agonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of the active compound per mililiter of formulation will constitute a therapeutically effective concentration for total application. If administered systemically, an amount between 0.01 and 5 mg per kg per day of body weight would be expected to effect a therapeutic result.

General Embodiments and Synthetic Methodology

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Unless specified otherwise, lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo- lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 or 2 is —COOH, this term covers the products derived from treatment of this function with alcohols or thiols preferably with aliphatic alcohols having 1–6 carbons. Where the ester is derived from compounds where B is —$CH_2OH$, this term covers compounds derived from organic acids capable of forming esters including phosphorous based and sulfur based acids, or compounds of the formula —$CH_2OCOR_{11}$ where $R_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where K is (—OR)$_2$. Here, R is lower alkyl. Also, K may be —$OR_7O$— where $R_7$ is lower alkyl of 2–5 carbon atoms, straight chain or branched.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Many compounds of the present invention have trans and cis (E and Z) isomers. Specific orientation of substituents relative to a double bond is indicated in the name of the respective compound, and/or by specifically showing in the structural formula the orientation of the substituents relative to the double bond. Unless it is specifically stated otherwise the invention covers trans as well as cis isomers.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

The compounds of the invention, can generally speaking be obtained by a series of reactions performed on the compounds of Formula 3

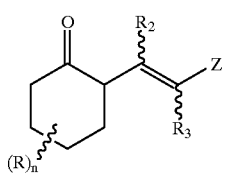

Formula 3 where Z is iodine (I) or trimethylsilyl and the remaining symbols have the meaning assigned to them in connection with Formulas 1 and 2. The cyclohexan-1-one derivatives of Formula 3 can, generally speaking, be readily obtained from compounds described in U.S. Pat. No. 5,760,276 the specification of which is incorporated herein by reference. An example of a compound within the scope of Formula 3, is 2-(2-iodoethenyl)-3-methyl-2-cyclohexan-1-one (Z=I) that can be obtained from the corresponding trimethylsilyl derivative (Z=trimethylsilyl) by treatment with iodone. The trimethylsilyl derivative of Formula 3 can be obtained by reduction of the corresponding cyclohexen-1-one that is available in accordance with U.S. Pat. No. 5,760,276. Another example of a compound within the scope of Formula 3 that is utilized for the synthesis of preferred compounds of the invention is 2-(2-[(trimethylsilyl)ethenyl]-3,3-dimethyl-2-cyclohexan-1-one (Z=trimethylsilyl, R=CH$_3$ and n=2) and the corresponding iodo derivative (Z=I) which can be obtained by reacting 2-[2-(trimethylsilyl)ethenyl]-3-methyl-2-cyclohexen-1-one with methyllithium and copper (I) iodide under conditions described in the '276 patent, and in case of the iodo derivative by susbsequent treatment with iodine.

In accordance with a generalized methodology for obtaining compounds of the invention the compounds of Formula 3, or readily available derivatives thereof, are reacted with an ethynyl-aryl or ethynyl heteroaryl derivative of the formula HC≡C—Y(R)—A—B in the presence of a suitable catalyst to obtain compounds of the invention where the X group is C≡C. The symbols Y, R, A and B are defined as in connection with Formulas 1 and 2.

To obtain compounds of the invention where the X group is —(CR=CR)$_n$—, generally speaking, a compound of Formula 3 where Z is iodine (I) is reacted with 1-(tributylstanny)-1-ethoxyethene followed by one or more Horner Emmons or Wittig reaction to provide a polyene chain. Thereafter, the ketone function of the cyclohexanone moiety is enolized by treatment with an acid anhydride, or trifluoromethanesulfonic acid anhydride in the presence of base. The trifluoromethanesulfonyl derivative can be converted to compounds of Formula 2 where $W_1$ is COOR$_2$ by treatment with carbon monoxide in an alcohol R$_2$OH (such as methanol), in the presence of a triphenylphoshine and palladium(II)acetate catalyst.

Compounds of the invention where the X group is COO, COS, or CONH can, generally speaking, be obtained by reacting a compound of Formula 3 where Z is iodine (I) with carbon monoxide and an aryl or heteroaryl reagent having a formula selected from HO—Y(R)—A—B, HS—Y(R)—A—B, and H$_2$N—Y(R)—A—B (the symbols Y, R, A and B are defined as in connection with Formulas 1 and 2) in the presence of triphenylphosphine and palladium (II) acetate catalyst.

The synthetic methodology employed for the synthesis of the compounds of the present invention may also include transformations of the group designated B in Formulas 1, and 2, and of the group W$_2$ in Formula 2. Generally speaking, these transformations involve reactions well within the skill of the practicing organic chemist. In this regard the following well known and published general principles and synthetic methodology are briefly described.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups,* Ed. Greene, John Wiley & Sons, 1981.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swem, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Specific Embodiments

With reference to the symbol Y in Formulas 1 and 2 the preferred compounds of the invention are those where Y is phenyl, naphthyl, pyridyl, thienyl or furyl. Even more preferred are compounds where Y is phenyl. As far as substitutions on the Y (phenyl) and Y (pyridyl) groups are concerned, compounds are preferred where the phenyl group is 1,4 (para) substituted and where the pyridine ring is 2,5 substituted. (Substitution in the 2,5 positions in the "pyridine" nomenclature corresponds to substitution in the 6-position in the "nicotinic acid" nomenclature.) In the presently preferred compounds of the invention there is no R substituent on the Y group.

The A-B group of the preferred compounds is $(CH_2)_q COOH$ or $(CH_2)_q—COOR_8$, where $R_8$ is defined as above. Even more preferably q is zero and $R_8$ is lower alkyl, (trialkylsilyl)alkyl or trialkylsilyl. Among the trialkylsilyl groups trimethylsilyl is preferred. Among the (trialkylsilyl)alkyl groups (trimethylsilyl)ethyl is preferred.

In the presently preferred compounds of the invention X is an ethynyl (—C≡C—) group. However, compounds are also preferred in accordance with the invention where X is —(CR=CR)$_n$—, —CO—NR—, COO and COS—.

The $W_1$ group of the compounds of Formula 1 is preferably —O—, and the $R_1$ group is preferably RCO, trifluoromethanesulfonyl or trialkylsilyl. Among the RCO groups acetyl, and among the trialkylsilyl groups trimethylsilyl are preferred. The $W_2$ group of the compounds of Formula 2 is preferably $COOR_2$, and among the $COOR_2$ groups COOMe is preferred.

The cyclohexene ring of the compounds of the invention is preferably methyl substituted (the R group in Formulas 1 and 2 in the ring is preferably methyl), and geminal dimethyl substitution in the ring is even more preferred.

The most preferred compounds of the invention are disclosed in Table 2 with reference to Formula 4.

Formula 4

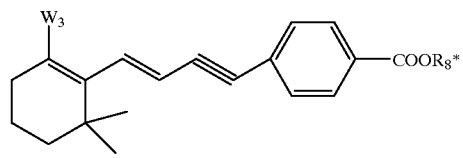

TABLE 2

| Compound # | $W_3$ | $R_{8^*}$ |
|---|---|---|
| 1 | —(CH$_3$)$_3$SiO— | ethyl |
| 2 | CH$_3$COO— | ethyl |
| 3 | CH$_3$COO— | —CH$_2$CH$_2$TMS[1] |
| 4 | CF$_3$SO$_3$— | —CH$_2$CH$_2$TMS[1] |
| 5 | CF$_3$SO$_3$— | ethyl |
| 6 | —CO$_2$CH$_3$ | ethyl |

[1]TMS is trimethylsilyl

The compounds of this invention can be made by the general procedures outlined above under the title "GENERAL EMBODIMENTS AND SYNTHETIC METHODOLOGY". The following chemical pathways represent the presently preferred synthetic routes to certain classes of the compounds of the invention and to certain specific exemplary compounds. However, the synthetic chemist will readily appreciate that the conditions set out here for these specific embodiments can be generalized to any and all of the compounds represented by Formulas 1 and 2.

REACTION SCHEME 1

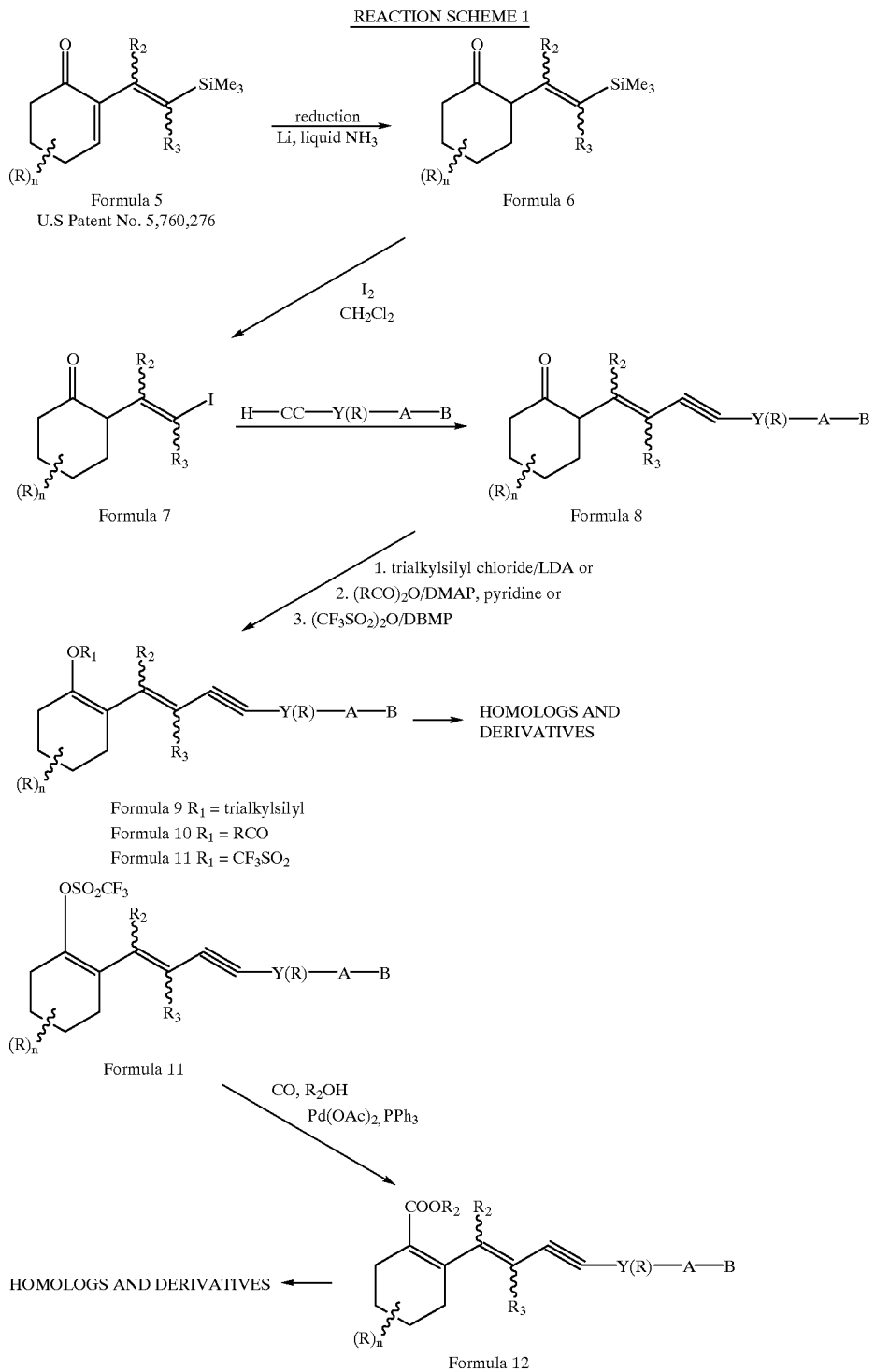

Formula 5 U.S Patent No. 5,760,276
Formula 6
Formula 7
Formula 8

Formula 9 R$_1$ = trialkylsilyl
Formula 10 R$_1$ = RCO
Formula 11 R$_1$ = CF$_3$SO$_2$ Formula 11
Formula 12

HOMOLOGS AND DERIVATIVES

Referring now to Reaction Scheme 1 a synthetic process is described whereby compounds of the invention are obtained in which, with reference to Formulas 1 and 2 the X group is an ethynyl (—C≡C—) function. The starting compounds indicated in this scheme are 2-[2-(trimethyl)silylethenyl]-2-cyclohexen-1-one derivatives of Formula 5 which can be obtained in accordance with the teachings of U.S. Pat. No. 5,760,276. The endocyclic double bond of the 2-[2-(trimethylsilyl)ethenyl]-2-cyclohexen-1-one derivative of Formula 5 is reduced with a reducing agent to provide a 2-[2-(trimethylsilyl)ethenyl]-2-cyclohexan-1-one derivative of Formula 6. Reducing agents which are generally known in the art to be suitable for the selective reduction of the double bond of enone compounds are, generally speaking, suitable for this reaction. Lithium metal in liquid ammonia, serves as an example, as is indicated in the reaction scheme.

The 2-[2-(trimethylsilyl)ethenyl]-2-cyclohexan-1-one derivatives of Formula 6 are then reacted with iodine in methylene chloride to provide 2-(2-iodoethenyl)-2-cyclohexan-1one derivatives of Formula 7. The latter iodo compounds are then reacted with an ethynyl-aryl or ethynyl-heteroaryl reagent of the formula HC≡C—Y(R)—A—B to provide 1-aryl or 1-heteroaryl 4-(cyclohexan-1-one-2-yl) but-1-yn-3-ene derivatives of Formula 8. The reagents HC≡C—Y(R)—A—B can be obtained in accordance with the teachings of U.S. Pat. No. 5,760,276 and their reactions with the iodo compounds of Formula 7 are also conducted in accordance with the teachings disclosed in that patent. The 1-aryl or 1-heteroaryl 4-(cyclohexan-1-one-2-yl)but-1-yn-3-ene derivatives of Formula 8 are converted to compounds of the invention by reaction with a trialkylsilyl chloride (such as trimethylsilyl chloride) after treatment with a base such as LDA, or by reaction with an acyl anhydride (such as acetic anhydride) in the presence of dimethylaminopyridine (DMAP) and pyridine, or as still another alternative by reaction with trifluoromethane-sulfonic anhydride in the presence of 2,6-di-tert-butyl-4-methylpyridine (DBMP). In these reactions the ketone function of the cyclohexanone ring is enolized to provide 1-aryl or 1-heteroaryl 4-(1-(trialkylsilyl)oxycyclohex-1-en-2-yl) but-1-yn-3-ene derivatives of Formula 9, 1-aryl or 1-heteroaryl 4-(1-acyloxy-cyclohex-1-en-2-yl)-but-1-yn-3-ene derivatives of Formula 10, and 1-aryl or 1-heteroaryl 4-(1-(trifluoromethanesulfonyl)oxycyclohex-1-en-2-yl)but-1-yn-3-ene derivatives of Formula 11, respectively. The compounds of Formulas 9, 10 and 11 are within the scope of the invention, particularly within the scope of Formula 1. These compounds can also be converted to further compounds of the invention by reactions well known to those skilled in the art. This is indicated in the reaction scheme by conversion to "homologs and derivatives".

Referring still to Reaction Scheme 1, the compounds of Formula 11 are reacted with carbon monoxide, an alcohol, such as methyl alcohol, in the presence of palladium(II) acetate and triphenylphosphine catalyst to provide 1-aryl or 1-heteroaryl 4-(1-carboalkoxycyclohex-1-en-2-yl)but-1-yn-3-ene derivatives of Formula 12. The compounds of Formula 12 are within the scope of the invention and particularly within the scope of Formula 2.

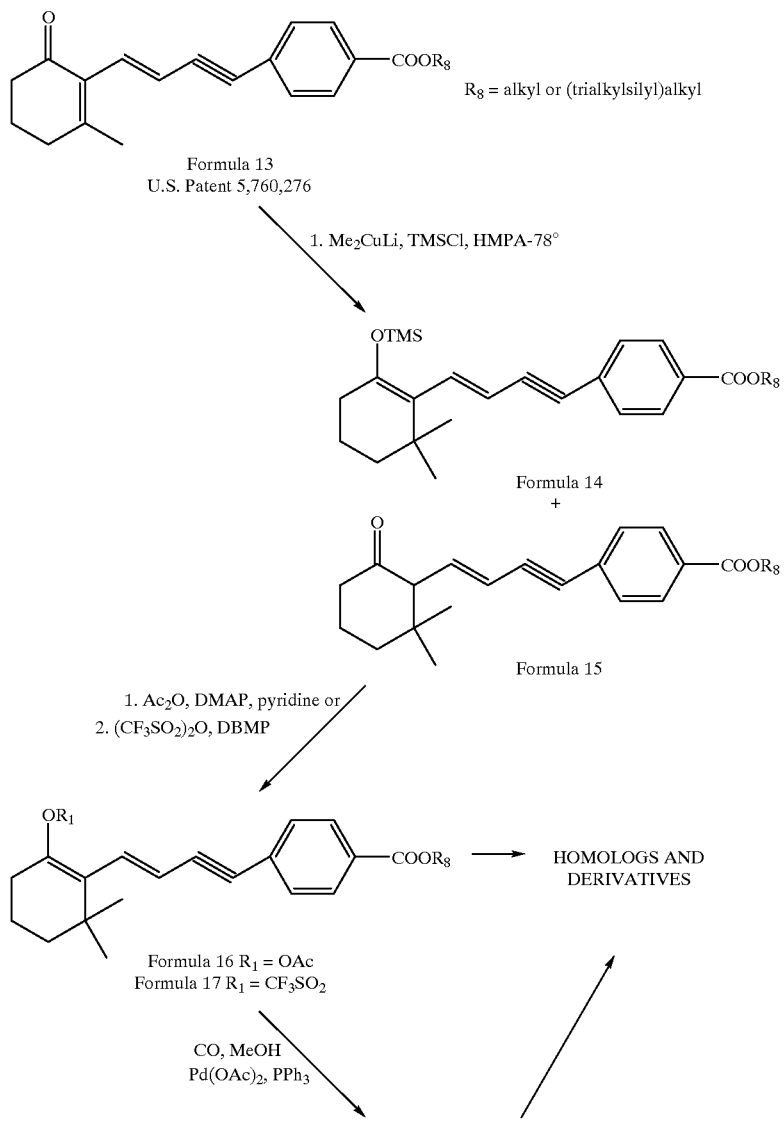

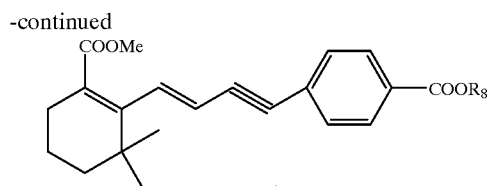

Formula 18

Reaction Scheme 2 discloses a synthetic route to certain preferred compounds of the invention where the cyclohexane ring is disubstituted with geminal dimethyl groups in a ring carbon α to the but-1-yn-3-ene moiety. The starting compound in this scheme is an alkyl or (trialkylsilyl)alkyl 4-(4-(2-methyl-6-oxocyclohex-1-enyl)but-3-en-1-ynyl) benzoate of Formula 13, that can be obtained in accordance with the teachings of U.S. Pat. No. 5,760,276. The starting compound of Formula 13 is reacted with methyllithium in the presence of copper (I) iodide, hexamethylphosphoramide and chlorotrimethylsilane and an acid acceptor such as pyridine. 3,3-dimethyl-1-(trimethylsilyl)oxycyclohex-1-ene derivatives of Formula 14 as well as the 3,3-dimethylcyclohexan-1-one derivatives of Formula 15 can both be made under such conditions. The compounds of Formula 14 are within the scope of the invention, as defined by Formula 1. The 3,3-dimethylcyclohexan-1-one derivatives of Formula 15 are treated with acetic anhydride in pyridine and in the presence of dimethylaminopyridine (DMAP) to provide the alkyl or (trialkylylsilyl)alkyl 4-(4-(1-acetyloxy-3,3-dimethylcyclohex-1-en-2-yl)but-3-en-1-ynyl)benzoate derivatives of Formula 16 ($R_1$ is OAc in Reaction Scheme 2). Alternatively, the compounds of Formula 15 are treated with trifluoromethanesulfonic anhydride in the presence of an acid acceptor, such as 2,6-di-tert-butyl-4-methylpyridine (DBMP) to provide the alkyl or (trialkylylsilyl)alkyl 4-(4-(1-(trifluoromethanesulfonyl)oxy-3,3-dimethyl-cyclohex-1-en-2-yl)but-3-ene-1-ynyl) benzoate derivatives of Formula 17 ($R_1$ is $CF_3SO_2$ in Reaction Scheme 2). The (trifluoromethanesulfonyl)oxy group of the compounds of Formula 17 is converted to an alkoxycarbonyl group, such as methoxycarbonyl that is shown in the reaction scheme, by treatment of the compounds of Formula 17 with carbon monoxide, and an alcohol (such as methanol) in the presence of palladium(II) acetate and triphenylphosphine catalyst. The resulting alkyl or (trialkylylsilyl)alkyl 4-(4-(1-alkoxycarbonyl-3,3-dimethylcyclohex-1-en-2-yl)but-3-en-1-ynyl)benzoate derivatives of Formula 18 are within the scope of the invention as defined by Formula 2, and can also be converted into further homologs and derivatives. Deesterification of the carboxyl groups can be accomplished by treatment with base (such as lithium hydroxide) when $R_8$ is alkyl, and by treatment with triethylammonium fluoride hydrate when $R_8$ is trialkylsilyl or (trialkylsilyl)alkyl.

REACTION SCHEME 3

-continued

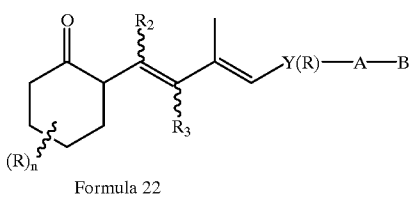

Formula 22

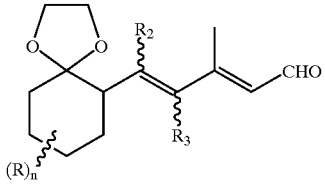

Formula 26

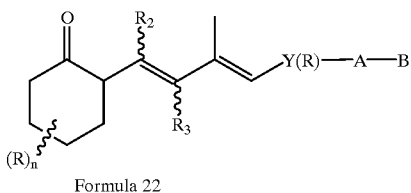

Formula 22

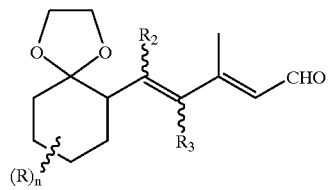

Formula 26

1. trialkylsilyl chloride/LDA or
2. (RCO)$_2$O/DMAP, pyridine or
3. (CF$_3$SO$_2$)$_2$O/DBMP

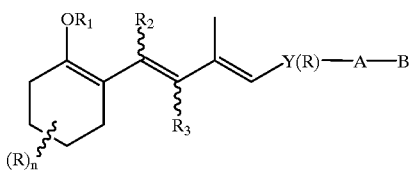

Formula 23 R$_1$ = trialkylsilyl
Formula 24 R$_1$ = RCO
Formula 25 R$_1$ = CF$_3$SO$_2$ 1. (OEt)$_2$PO ... COOEt  LDA Compound A 2. acid

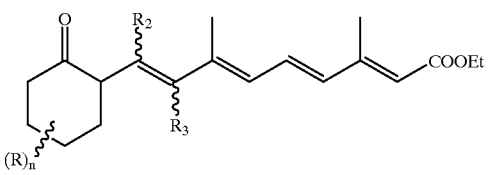

Formula 27

1. trialkylsilyl chloride/LDA, or
2. (RCO)$_2$O/DMAP, pyridine or
3. (CF$_3$SO$_2$)$_2$O/DBMP

HOMOLOGS AND DERIVATIVES

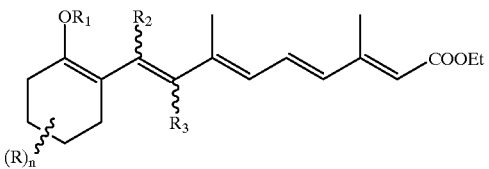

Formula 28 R$_1$ = trialkylsilyl
Formula 29 R$_1$ = RCO
Formula 30 R$_1$ = CF$_3$SO$_2$ Reaction Scheme 3 discloses an exemplary synthetic route for preparation of compounds of the invention where the X group in Formula 1 and 2 is (CR=CR)$_{n'}$. The starting compounds in this scheme are 2-(2-iodoethenyl)-2-cyclohexan-1-one derivatives of Formula 7 that can be obtained as shown in Reaction Scheme 1. The ketone function of the iodo compounds of Formula 7 is protected by conversion to a cyclic ketal by treatment with ethylene glycol in the presence of acid, to provide the dioxolane (ketal) derivatives of Formula 19.

The protected dioxolane (ketal) derivatives of Formula 19 are reacted with (1-ethoxyvinyl)tributyltin in the presence of bis(triphenylphosphine)palladium(II) chloride to introduce the acetyl group adjacent to the vinyl group and to yield the compounds of Formula 20. The latter reaction is known in the art as a Stille coupling. (1-ethoxyvinyl)tributyltin is available from Aldrich Chemical Co.) The compounds of Formula 20 are reacted with a Horner Emmons reagent of the formula (EtO)$_2$POCH$_2$—Y(R)—A—B in the presence of strong base such as lithium diisopropylamide (LDA). The symbols Y, R, A and B for the reagent (EtO)$_2$POCH$_2$—Y(R)—A—B are defined as in connection with Formulas 1 and 2. Examples for the reagents (EtO)$_2$POCH$_2$—Y(R)—A—B are: ethyl [4-(diethoxyphosphinyl)methyl]benzoate, ethyl [6-(diethoxyphosphinyl)methyl]pyridine-3-carboxylate, ethyl [5-(diethoxyphosphinyl)methylfuran-2-carboxylate and ethyl [5-(diethoxyphosphinyl)methylthiophen-2-carboxylate. These reagents can be obtained in accordance with or in analogy to the process described in U.S. Pat. No. 5,455,265 for the synthesis of ethyl [4-(diethoxyphosphinyl)methyl]benzoate and ethyl [5-(diethoxyphosphinyl)methylfuran-2-carboxylate. The specification of U.S. Pat. No. 5,455,265 is incorporated herein by reference. The products of the Horner Emmons reaction with the reagent (EtO)$_2$POCH$_2$—Y(R)—A—B are thereafter treated with acid to remove the dioxolane protective group and to provide the 1-aryl or 1-heteroaryl 4-(cyclohexan-1-on-2-yl) butadiene derivatives of Formula 22.

Referring still to Reaction Scheme 3, the enone compounds of Formula 20 can also be reacted in a Horner Emmons reaction, in the presence of strong base (lithium diisopropylamide, LDA) with diethyl cyanomethylphosphonate. The latter reagent is commercially available. The products of this Horner Emmons reaction are 4-cyclohexanonyl-1-cyano-2-methyl-butadiene derivatives of Formula 21 in which the ketone is still protected as a cyclic ketal. Those skilled in the art will readily understand that instead of a Horner Emmons reaction the compounds of Formulas 21 and/or 22 can also be obtained as a result of analogous Wittig reactions. The cyano function of the compounds of Formula 21 is reduced by treatment with a mild reducing agent, such as diisobutylaluminum hydride (Dibal-H) to provide the aldehyde compounds of Formula 26. Another Horner Emmons reaction performed on the aldehydes of Formula 26 with the reagent diethyl (E)-3-carboethoxy-2-methyl-1-allylphosphonate (Compound A) in the presence of strong base (LDA) provides, after removal of the cyclic ketal protective group, the 1-ethoxycarbonyl-6-(cyclohexan-1-on-2-yl-octatetraene derivatives of Formula 27.

Referring still to Reaction Scheme 3, the 1-aryl or 1-heteroaryl 4-(cyclohexan-1-on-2-yl) butadiene derivatives of Formula 22 are converted to compounds of the invention by reaction with a trialkylsilyl chloride (such as trimethylsilyl chloride) and LDA or by reaction with an acyl anhydride (such as acetic anhydride) in the presence of dimethylaminopyridine and pyridine, or as still another alternative by reaction with trifluoromethanesulfonic anhydride in the presence of 2,6-di-tert-butyl-4-methylpyridine (DBMP), in analogy to the like reactions described in connection with Reaction Scheme 1. In these reactions the ketone function of the cyclohexanone ring is enolized to provide 1-aryl or 1-heteroaryl 4-(1-(trialkylsilyl)oxycyclohex-1-en-2-yl) butadiene derivatives of Formula 23, 1-aryl or 1-heteroaryl 4-(1-acyloxycyclohex-1-en-2-yl)butadiene derivatives of Formula 24, and 1-aryl or 1-heteroaryl 4-(1-(trifluoromethanesulfonyl)oxycyclohex-1-en-2-yl) butadiene derivatives of Formula 25, respectively. The compounds of Formulas 23, 24 and 25 are within the scope of the invention, particularly within the scope of Formula 1. Although this is not shown in Reaction Scheme 3, the trifluoromethanesulfonyl derivatives of Formula 25 are reacted with carbon monoxide, and an alcohol, such as methyl alcohol, in the presence of palladium(II) acetate and triphenylphosphine catalyst to provide 1-aryl or 1-heteroaryl 4-(1-carboalkoxycyclohex-1-en-2-yl)butadiene derivatives of the invention within the scope of Formula 2.

The 1-ethoxycarbonyl-6-(cyclohexan-1-on-2-yl- or 6-(cyclohex-1-on-2-en-2-yl)octatetraene derivatives of Formula 27 are treated with a trialkylsilyl chloride, or with an acyl anhydride, or as still another alternative with trifluoromethanesulfonic anhydride in analogy to the like reactions described in connection with the compounds of Formula 22, to provide the 1-aryl or 1-heteroaryl 4-(1-carboalkoxycyclohex-1-en-2-yl)octatetraene derivatives of Formulas 28–30. The compounds of Formula 30 are also reacted (not shown in the scheme) with carbon monoxide, an alcohol, such as methyl alcohol, in the presence of palladium (II) acetate and triphenylphosphine catalyst to provide 1-aryl or 1-heteroaryl 4-(1-carboalkoxycyclohex-1-en-2-yl) octatetraene derivatives of the invention within the scope of Formula 2.

The compounds of Formulas 23–25 and 28–30 can be converted into further compounds also within the scope of the invention by reactions well known in the art. This is indicated in the reaction scheme by conversion to "homologs and derivatives".

The reagent diethyl (E)-3-carboethoxy-2-methyl-1-allylphosphonate (Compound A) is obtained in a sequence of reactions starting from the commercially available ethyl (Z)-3-formyl-2-butenoate (Compound B). In this preparation the aldehyde function of Compound B is reduced with sodium borohydride, and the resulting primary alcohol is reacted with phosphorous tribromide. The resulting ethyl (Z)-3-bromo-2-butenoate is reacted with triethyl phosphite to give Compound A.

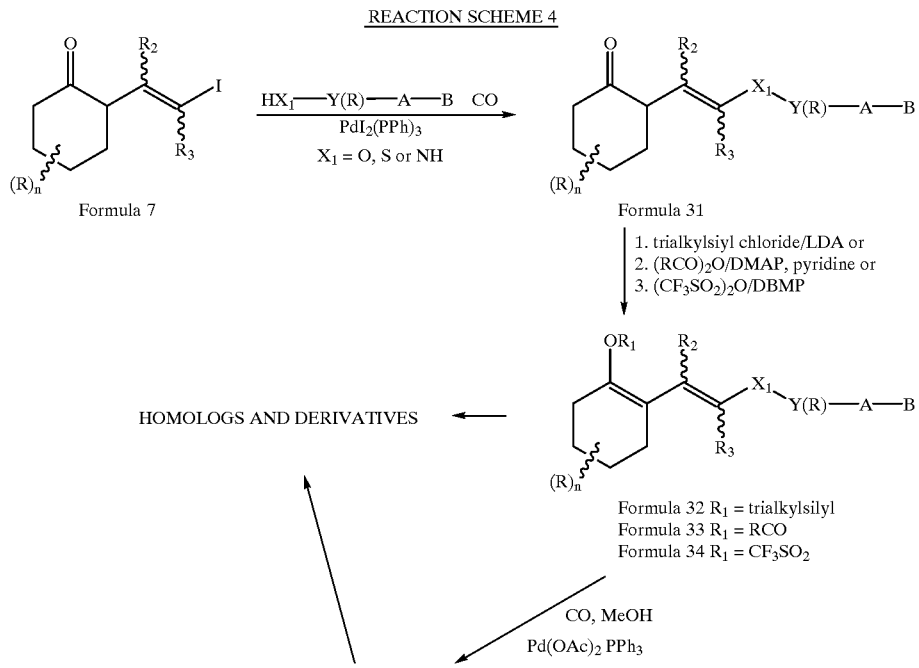

-continued

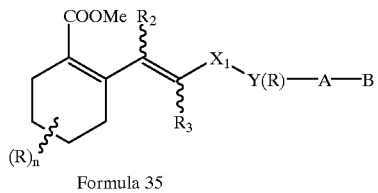

Formula 35

Exemplary processes to obtain compounds of the invention where with reference to Formulas 1 and 2 the X group is C(O)O, C(O)S, CONR, or CSNR are disclosed in Reaction Scheme 4. These compounds of the invention can be made by reacting the 2-(2-iodoethenyl)-2-cyclohexan-1-one derivatives of Formula 7 (obtained as indicated in Reaction Scheme 1) with a reagent of the formula $HX_1$,—Y(R)—A—B and carbon monoxide (CO) in the presence of tris (triphenylphosphine)palladium(II) iodide catalyst in analogy to the reactions described in the treatise Heck, Richard F. "Palladium Reagents in Organic Synthesis" Academic Press (Orlando Fla.) 1985, pp 374–381, incorporated herein by reference. The symbol $X_1$ in the formula of the reagent $HX_1$,—Y(R)—A—B represents O, S, or NH, thus the reagents are hydroxyl, thiol or primary amine derivatives of aryl and heteroaryl compounds. Examples for these reagents are ethyl 4-hydroxybenzoate, ethyl 4-mercaptobenzoate, ethyl 4-aminobenzoate, ethyl 6-hydroxynicotinoate, ethyl 6-aminonicotinoate, ethyl 5-hydroxy-furan-2-carboxylate, ethyl 5-aminofuran-2-carboxylate, ethyl 5-hydroxythiophen-2-carboxylate and ethyl 5-aminothiophen-2-carboxylate. The resulting compounds of Formula 31 are treated with a trialkylsilyl chloride, or with an acyl anhydride, or as still another alternative with trifluoromethanesulfonic anhydride in analogy to the like reactions described above (for example in connection with the compounds of Formula 22) to provide compounds of the invention shown in Formulas 32–34. The trifluoromethanesulfonyloxy derivative of Formula 34 is converted to the methoxycarbonyl derivative of the invention of Formula 35. The compounds of the invention shown by Formulas 32–35 can be converted into further homologs and derivatives as is indicated in the scheme.

Analogs of the above described exemplary compounds of the invention where with reference to Formula 1 the $W_1$ group is S can be obtained in synthetic schemes where the intermediate cyclohexanone compounds is first converted to the corresponding thione, by treatment with a thiolating agent such as Lawesson's Reagent or phosphorous pentasulfide, followed by the steps described above with respect to the intermediates having the cyclohexanone moiety.

SPECIFIC EXAMPLES (Trimethylsilyl)ethyl 4-ethynylbenzoate (Compound C)

A solution of (trimethylsilyl)ethyl 4-iodobenzoate (2.5 g, 7.2 mmol), (tributyltin)acetylene (2.5 mL, 8.6 mmol) and THF (50 mL) was purged with argon for 10 minites, and then treated with bis(triphenylphosphine)palladium (II) chloride (126 mg, 0.18 mmol). The suspension was stirred overnight at room temperature and then for 1 hour at 50° C. The solution was treated with $NH_4Cl$ and the product extracted with 50% ethyl acetate and hexane solution. The layers were separated and the aqueous layer extracted twice more with the same organic solution. The combined organic layers were washed with brine, and dried ($MgSO_4$), filtered and the solvents were removed under reduced pressure. The residue was purified by silica gel chromatography (98:2, hexane:ethyl acetate) to give the title compound as a yellow oil. PNMR (300 MHz, $CDCl_3$) δ0 0.08 (s, 9H), 1.13 (t, 2H, J=8.5 Hz), 3.21 (s, 1 H), 4.17 (t, 2H, J=8.5 Hz), 7.54 (d, 2H, J=8.3 Hz), 7.99 (d, 2H, J=8.3 Hz).

(Trimethylsilyl)ethyl 4-(4-(2-methyl-6-oxocyclohex-1-enyl)-but-3-en-1-yn-yl)benzoate Compound D A solution of 1-iodo-2-(2-methyl-6-oxocyclohex-1-enyl) ethene (Compound E, available in accordance with the teachings of U.S. Pat. No. 5,760,276, 0.70 g, 2.67 mmol), (trimethylsilyl)ethyl 4-ethynylbenzoate (Compound C, 0.79 g, 3.21 mmol) and triethylamine (32 mL) was purged with argon for 10 minutes, and then treated with bis (triphenylphosphine)palladium (II) chloride (47 mg, 0.07 mmol) and copper (I) iodide (12.8 mg, 0.07 mmol). The solution was stirred 40° C. for 3 hours, and concentrated under a water aspirator vacuum. The residue was dissolved in ethyl acetate and washed with saturated aqueous $NH_4Cl$. The layers were separated and the aqueous layer was extracted twice with ethyl acetate. The combined organic fractions were washed with water, and brine, and dried ($MgSO_4$). The solvents were removed under reduced pressure, and the residue was purified by silica gel chromatography (90:10, hexane:ethyl acetate) to give the title compound.

PNMR (300 MHz, $CDCl_3$) δ6 0.08 (s, 9H), 1.13 (t, 2H, J=8.5 Hz), 1.97 (m, 2H), 2.10 (s, 3H), 2.47 (m, 4H), 4.41 (t, 2H, J=8.5 Hz), 6.40 (d, 1H, J=15 Hz), 6.84 (d, 1H, J=15 Hz), 7.49 (d, 2H, J=8.3 Hz), 7.97 (d, 2H, J=8.3 Hz).

Ethyl 4-ethynylbenzoate

Compound F

A solution of ethyl 4-iodobenzoate (6.9 g, 25 mmol), (trimethylsilyl)acetylene (7.1 mL, 50 mmol) and triethylamine (200 mL) was purged with argon for 10 minutes, and then treated with bis(triphenylphosphine)palladium (II) chloride (175 mg, 0.25 mmol) and copper (I) iodide (48 mg, 0.25 mmol). The suspension was stirred at room temperature for 3 hours and concentrated under the vacuum of a water aspirator. The residue was dissolved in hexane and washed with 10% aqueous HCl. The layers were separated and the aqueous layer was extracted twice with hexane. The combined organic fractions were washed with water, and brine. The separated organic layer was treated directly with 1 M solution of tetrabutylammonium fluoride and THF (35 mL, 35 mmol). After 30 minutes, the solution was washed with water (2x), and brine, dried ($MgSO_4$) and filtered through silica gel. The solvents were removed under reduced pressure and the residue was purified by silica gel chromatography (98:2, hexane:ethyl acetate) to give the title compound as a yellow oil.

PNMR (300 MHz, CDCl$_3$) δ1.39 (t, 3H, J=7.1 Hz), 3.24 (s, 1H), 4.38 (q, 2H, J=7.1 Hz), 7.54 (d, 2H, J=8.3 Hz), 7.99 (d, 2H, J=8.3 Hz).

(Trimethylsilyl)ethyl (±)-(E)-4-(4-(2,2-dimethyl-6-oxocyclohexyl)but-3-en-1-yn-yl)benzoate Compound G A 1.3 M solution of methyllithium (3.8 mL, 5.26 mmol) was added to a stirring suspension of copper (I) bromide-dimethyl sulfide (541 mg, 2.63 mmol) and 10 mL of THF at −78° C. The solution was warmed to −40° C. over 30 minutes and then re-cooled to −78° C. Freshly distilled hexamethylphosphoramide (0.685 mL, 3.94 mmol) was added, and the solution was stirred at −78° C. for 30 minutes. A solution of (trimethylsilyl)ethyl 4-(4-(2-methyl-6-oxocyclohex-1-enyl)but-3-en-1-ynyl)benzoate (Compound D, 500 mg, 1.31 mmol), chlorotrimethylsilane (0.50 mL, 3.94 mmol) and 2.5 mL of THF was added. After the solution was stirred at −78° C. for 1 hour, pyridine (0.159 mL) and ether (0.5 mL) were added. The reaction was then quenched by the addition of 5% aqueous NaHCO$_3$. The layers were separated and the aqueous layer extracted 3 times with ethyl acetate. The combined organic layers were washed with 10% aqueous HCl until all of the enol ether was hydrolyzed. The layers were separated and the organic layer was washed with water, and brine, and dried (MgSO$_4$). The solvents were removed under reduced pressure, and the residue was purified by silica gel chromatography (10:1, hexane:ethyl acetate) to give the title compound as a yellow solid.

PNMR (300 MHz, CDCl$_3$) δ0.08 (s, 9H), 0.89 (s, 3H), 1.03 (s, 3H), 1.13 (m, 2H), 1.69 (m, 2H), 1.94 (m, 2H), 2.39 (m, 2H), 2.89 (d, 1H, J=9.9 Hz), 4.41 (m, 2H), 5.69 (d, 1H, J=15.9 Hz), 6.40 (dd, 1H, J=9.9, 15.9 Hz), 7.48 (d, 2H, J=8.4 Hz), 7.97 (d, 2H, J=8.4 Hz).

Ethyl 4-(4-(2-methyl-6-oxocyclohex-1-enyl)but-3-en-1-ynyl)benzoate

Compound H

A solution of 2-(2-methyl-6-oxocyclohex-1-enyl)-1-iodoethene (Compound E, 1.74 g, 6.64 mmol), ethyl 4-ethynylbenzoate (Compound F, 1.73 g, 9.96 mmol) and triethylamine (80 mL) was purged with argon for 10 minutes, and then treated with bis(triphenylphosphine) palladium (II) chloride (23 mg, 0.03 mmol) and copper (I) iodide (6.3 mg, 0.03 mmol). The solution was stirred 40° C. for 3 hours, and concentrated under a water aspirator vacuum. The residue was dissolved in ethyl acetate and washed with saturated aqueous NH$_4$Cl. The layers were separated and the aqueous layer was extracted twice with ethyl acetate. The combined organic fractions were washed with water, and brine, and dried (MgSO$_4$). The solvents were removed under reduced pressure, and the residue was purified by silica gel chromatography (88:12, hexane:ethyl acetate) to give the title compound as a yellow crystalline solid.

PNMR (300 MHz, CDCl$_3$) δ1.39 (t, 3H, J=7.1 Hz), 1.97 (m, 2H), 2.11 (s, 3H), 2.45 (m, 4H), 4.37 (q, 2H, J=7.1 Hz), 6.58 (d, 1H, J=16.4 Hz), 6.85 (d, 1H, J=16.4 Hz), 7.49 (d, 2H, J=8.5 Hz), 7.98 (d, 2H, J=8.5 Hz).

Ethyl (±)-(E)-4-(4-(2,2-Dimethyl-6-oxocyclohexyl) but-3-en-1-ynyl)benzoate

Compound I 1.3 M solution of methyllithium (2.2 mL, 2.85 mmol) was added to a stirring suspension of copper (I) bromide-dimethyl sulfide (293 mg, 1.43 mmol) and 6 mL of THF at −78° C. The solution was warmed to −40° C. over 30 minutes and then recooled to −78° C. Freshly distilled hexamethylphosphoramide (0.37 mL, 2.14 mmol) was added, and the solution was stirred at −78° C. for 30 minutes. A solution of ethyl 4-(4-(2-methyl-6-oxocyclohex-1-enyl) but-3-en-1-ynyl)benzoate (Compound H, 220 mg, 0.713 mmol), chlorotrimethylsilane (0.271 mL, 2.14 mmol) and 1.5 mL of THF was added. The solution was stirred at −78° C. for 1 hour, and warmed slowly to −30° C. The reaction was then quenched by the addition of saturated aqueous NH$_4$Cl and ethyl acetate. The layers were separated and the aqueous layer extracted 3 times with ethyl acetate. The combined organic layers were washed with 10% aqueous HCl until all of the enol ether was hydrolyzed. The layers were separated and the organic layer was washed with water, and brine, and dried (MgSO$_4$). The solvents were removed under reduced pressure, and the residue was purified by silica gel chromatography (10:1, hexane:ethyl acetate) to give the title compound as a yellow oil.

PNMR (300 MHz, CDCl$_3$) δ0.88 (s, 3H), 1.02 (s, 3H), 1.38 (t, 3H, J=7.1 Hz), 1.66 (m, 2H), 1.91 (m, 2H), 2.37 (m, 2H), 2.88 (d, 1H, J=9.8 Hz), 4.36 (q, 2H, J=7.1 Hz), 5.68 (d, 1H, J=15.9 Hz), 6.39 (dd, 1H, J=9.8, 15.9 Hz), 7.47 (d, 2H, J=8.4 Hz), 7.98 (d, 2H, J=8.4 Hz).

Ethyl (±)-(E)-4-(4-(6,6-dimethyl-2-(trimethylsilyl) oxycyclohex-1-enyl)but-3-en-1-yn-yl)benzoate Compound 1

A 1.3 M solution of methyllithium (0.78 mL, 1.04 mmol) was added to a stirring suspension of copper (I) bromide-dimethyl sulfide (107 mg, 0.52 mmol) and 2 mL of THF at −78° C. The solution was warmed to −40° C. over 30 minuts and then re-cooled to −78° C. Freshly distilled hexamethylphosphoramide (0.091 mL, 0.52 mmol) was added, and the solution was stirred at −78° C. for 30 minutes. A solution of ethyl 4-(4-(2-methyl-6-oxocyclohex-1-enyl)but-3-en-1-ynyl)benzoate (Compound H, 80 mg, 0.26 mmol), chlorotrimethylsilane (0.07 mL, 3.94 mmol) and 2.5 mL of THF was added. After the solution was stirred at −78° C. for 1 hour, pyridine (0.020 mL) and ether (0.065 mL) were added. The reaction was then quenched by the addition of 5% aqueous NaHCO$_3$. The layers were separated and the aqueous layer was extracted 3 times with ethyl acetate. The solvents were removed under reduced pressure, and the residue was purified by silica gel chromatography (10:1, hexane:ethyl acetate) to give the title compound as a yellow solid.

PNMR (500 MHz, CDCl$_3$) δ0.23 (s, 9H), 1.15 (s, 6H), 1.39 (t, 3H, J=7.0 Hz), 1.46 (m, 2H), 1.67 (m, 2H), 2.18 (t, 2H, J=6.5 Hz), 4.37 (q, 2H, J=7.0 Hz), 6.19 (d, 1H, J=16.5 Hz), 6.79 (d, 1H, J=16.5 Hz), 7.47 (d, 2H, J=8.5 Hz), 7.97 (d, 2H, J=8.5 Hz).

Ethyl (±)-(E)-4-(4-(2-acetoxy-6,6-dimethylcyclohex-1-enyl)but-3-en-1-yn-yl)benzoate Compound 2

General Procedure A: Ethyl (±)-(E)-4-(4-(2,2-dimethyl-6-oxocyclohexyl)but-3-en-1-ynyl)benzoate (Compound I, 100 mg, 0.308 mmol) was dissolved in dichloromethane (2.5 mL) and treated with pyridine (0.623 mL, 7.71 mmol) and acetic anhydride (0.581 mL, 6.16 mmol). Dimethylaminopyridine (DMAP, 5 mg) was added and the solution was protected from light and stirred for 16 hours at room temperature. The solution was diluted with ethyl acetate and 10% aqueous H₃PO₄ was added. The layers were separated and the aqueous layer was extracted twice with ethyl acetate. The combined organic layers were washed with water, and brine, dried (Na₂SO₄), and filtered and the solvents were removed in vacuo. The residue was purified by silica gel chromatography using a solution of hexane and ethyl acetate in a 90 to 10 ratio, respectively, to give the title compound as a yellow oil.

PNMR (300 MHz, CDCl₃) δ1.14 (s, 6H), 1.39 (t, 3H, J=7.1 Hz), 1.51 (m, 2H), 1.73 (m, 2H), 2.15 (s, 3H), 2.23 (t, 2H, J=6.6 Hz), 4.37 (q, 2H, J=7.1 Hz), 5.97 (d, 1H, J=16.5 Hz), 6.53 (d, 1H, J=16.5 Hz), 7.48 (dd, 2H, J=6.7, 1.7 Hz), 7.99 (dd, 2H, J=6.7, 1.5 Hz).

(Trimethylsilyl)ethyl (±)-(E)-4-(4-(2-acetoxy-6,6-dimethylcyclohex-1-enyl)but-3-en-1-ynyl)benzoate Compound 3

The title compound was prepared from (trimethylsilyl) ethyl (±)-(E)-4-(4-(2,2-dimethyl-6-oxocyclohexyl)but-3-en-1-ynyl)benzoate (Compound G, 100 mg, 0.252 mmol) by using General Procedure A.

PNMR (300 MHz, CDCl₃) δ0.07 (s, 9H), 1.12 (m, 2H), 1.14 (s, 6H), 1.51 (m,2H), 1.73 (m, 2H), 2.14 (s, 3H), 2.22 (t, 2H, J=6.6 Hz), 4.40 (m, 2H), 5.97 (d, 1H, J=16.5 Hz), 6.53 (d, 1H, J=16.5 Hz), 7.47 (d, 2H, J=8.4 Hz), 7.97 (d, 2H, J=8.4 Hz).

(Trimethylsilyl)ethyl (E)-4-(4-(6,6-dimethyl-2-(trifluromethanesulfonyl)oxycyclohex-1-enyl)but-3-en-1-yn-yl)benzoate Compound 4

Trifluoromethanesulfonic anhydride (0.109 mL, 0.65 mmol) was added to a solution of (trimethylsilyl)ethyl (±)-(E)-4-(4-(2,2-dimethyl-6-oxocyclohexyl)but-3-en-1-ynyl)benzoate (Compound G, 150 mg, 0.38 mmol) and 2,6-di-tert-butyl-4-methylpyridine (DBMP, 218 mg, 1.06 mmol) in dichloromethane (4 mL). The flask was sealed with a plastic cap and stirred for 2 days at room temperature. The solution was diluted with ethyl acetate and washed with 10% aqueous H₃PO₄. The layers were separated and the aqueous layer extracted three times with ethyl acetate. The combined organic layers were washed with 5% aqueous NaHCO₃, and brine, and dried (Na₂SO₄). The solvents were removed under reduced pressure, and the residue was purified by silica gel chromatography (10:1, hexane:ethyl acetate) to give the title compounds as a 1:1 mixture of isomers. The compounds were separated by HPLC using a Whatman Partisil-10 1×50 cm column (95:5, hexane:ethyl acetate) to provide the title compound as a colorless oil:

PNMR (300 MHz, CDCl₃) δ0.09 (s, 9H), 1.14 (m, 2H), 1.17 (s, 6H), 1.55 (m, 2H), 1.79 (m, 2H), 2.45 (t, 2H, J=6.6 Hz), 4.42 (m, 2H), 6.09 (d, 1H, J=16.5 Hz), 6.55 (d, 1H, J=16.5 Hz), 7.51 (d, 2H, J=8.5 Hz), 7.99 (d, 2 H, J=8.5 Hz).

Ethyl (E)-4-(4-(2,2-dimethyl-6-(trifluromethanesulfonyl)oxycyclohex-1-en-yl)but-3-en-1-ynyl)benzoate (Compound 5) and ethyl (±)-(E)-4-(4-(2,2-dimethyl-6-(trifluromethanesulfonyl)oxycyclohex-5-enyl)but-3-en-1-yn-yl)benzoate Compound 6

Trifluoromethanesulfonic anhydride (0.135 mL, 0.80 mmol) was added to a solution of ethyl (±)-(E)-4-(4-(2,2-dimethyl-6-oxocyclohexyl)but-3-en-1-ynyl)benzoate (Compound I, 93 mg, 0.30 mmol) and 2,6-di-tert-butyl-4-methylpyridine (DBMP, 165 mg, 0.80 mmol) in dichloromethane (4.5 mL). The flask was sealed with a plastic cap and stirred for 3 days at room temperature. The solution was diluted with diethyl ether and washed with saturated NH₄Cl, 5% aqueous NaHCO₃ and brine, and dried (MgSO₄). The solvents were removed under reduced pressure, and the residue was purified by silica gel chromatography (10:1, hexane:ethyl acetate) to give the title compounds as a 1:1 mixture of isomers. The compounds were separated by HPLC using a Whatman Partisil-10 1×50 cm column (95:5, hexane:ethyl acetate) to provide ethyl (E)-4-(4-(2,2-dimethyl-6-(trifluromethanesulfonyl)oxycyclohex-1-enyl)but-3-en-1-ynyl)benzoate Compound 5

PNMR (300 MHz, CDCl₃) δ1.16 (s, 6H), 1.39 (t, 3H, J=7.1 Hz), 1.53 (m, 2H), 1.79 (m, 2H), 2.44 (m, 2H), 4.37 (q, 2H, J=7.1 Hz), 6.08 (d, 1H, J=16.5 Hz), 6.52 (d, 1H, J=16.5 Hz), 7.50 (d, 2H, J=8.4 Hz), 7.99 (dd, 2H, J=2.0, 8.4 Hz), and ethyl (±)-(E)-4-(4-(2,2-dimethyl-6-(trifluromethanesulfonyl)oxycyclohex-5-enyl)but-3-en-1-ynyl)benzoate Compound 6

PNMR (300 MHz, CDCl₃) δ0.95 (s, 3H), 1.04 (s, 3H), 1.25–1.58 (m, 4H), 1.39 (t, 3H, J=7.2 Hz), 2.23 (m, 2H), 2.76 (d, 1H, J=11.3 Hz), 4.37 (q, 2H, J=7.2 Hz), 5.82 (d, 1H, J=14.5 Hz), 5.86 (t, 1H, J=4.5 Hz), 6.08 (dd, 1 H, J=11.3, 14.5 Hz), 7.48 (d, 2H, J=8.3 Hz), 7.98 (d, 2H, J=8.3 Hz)).

Ethyl (E)-4-(4-(6-Carbomethoxy-2,2-dimethylcyclohex-1-enyl)but-3-en-1-yn-yl)benzoate Compound 7

Ethyl (E)-4-(4-(2,2-dimethyl-6-(trifluromethanesulfonyl) oxycyclohex-1-enyl)but-3-en-1-yn-yl)benzoate (Compound 5, 47 mg, 0.10 mmol) was dissolved in methanol (5 mL). The solution was treated with palladium (II) acetate (22.4 mg, 0.10 mmol), PPh₃ (45 mg, 0.17 mmol), triethylamine (0.78 mL), and DMF (12.5 mL). The solution was purged with carbon monoxide for 30 minutes and then kept under a balloon pressure of CO and stirred for 20 hours at room temperature and 3 hours at 50° C. The solution was diluted with diethyl ether and washed with water, and brine, and dried (MgSO₄). The solvents were removed under reduced pressure, and the residue was purified by silica gel chromatography (19:1/hexane:ethyl acetate) to give the title compound:

PNMR (300 MHz, CDCl₃) δ1.10 (s, 6H), 1.39 (t, 3H, J=7.1 Hz), 1.51(m, 2H), 1.67 (m, 2H), 2.31 (m, 2H), 3.70 (s, 3H), 4.37 (q, 2H, J=7.1 Hz), 5.72 (d, 1H, J=16.1 Hz), 6.78 (d, 1H, J=16.1 Hz), 7.49 (dd, 2H, J=1.7, 8.3 Hz), 7.99 (dd, 2H, J=1.7, 8.3 Hz).

What is claimed is:

1. A compound having the structure selected from formula (1) and formula (2)

formula (1)

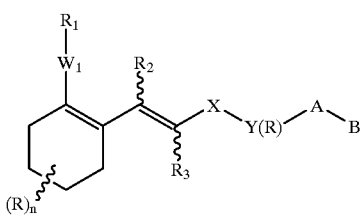

formula (2)

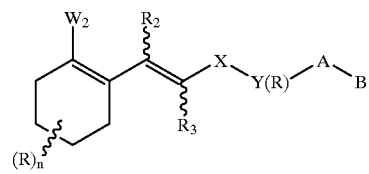

where $R_1$ is alkyl of 1 to 10 carbons, $(R_4)_p$-phenyl, RCO, or $C_1$–$C_6$ trialkylsilyl;

$W_1$ of Formula 1 is O or S with the proviso that $W_1$ is not S when $R_1$ is RCO;

$W_2$ of Formula 2 is $CH_2OR_2$, $R_2CO$, $CO_2R_2$ or $CON(R_2)_2$;

p is an integer having the values 0 to 5;

R is H, lower alkyl of 1 to 10 carbons, cycloalkyl of 3 to 10 carbons, halogen, $(C_{1-10}$-lower alkyl$)_3$-silyl, $C_{1-10}$-lower alkylphenyl, or phenyl-$C_{1-10}$-lower alkyl;

$R_2$ and $R_3$ independently are H, lower alkyl of 1 to 10 carbons, cycloalkyl of 3 to 10 carbons, $(C_{1-10}$-lower alkyl$)_3$-silyl, $C_{1-10}$-lower alkylphenyl, or phenyl-$C_{1-10}$-lower alkyl;

$R_4$ is alkyl of 1 to 10 carbons, F, Cl, Br, I, $NO_2$, $(CH_2)_pCOOH$, $(CH_2)_pCOOR$;

n is an integer having the values of 0 to 6;

X is $C\equiv C$, $C(O)O$, CONR, CSNR, and $(CR=CR)_{n'}$ where n' is an integer having the values 1 to 5;

Y is a phenyl or naphthyl group, said phenyl and naphthyl groups being optionally substituted with one or two R groups, or when X is —$(CR=CR)_{n'}$— and n' is 3, 4 or 5 then Y represents a direct valence bond between said $(CR=CR)_{n'}$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_3$ is divalent alkyl radical of 2–5 carbons, or a pharmaceutically acceptable salt of said compound.

2. A compound in accordance with claim 1 having the structure of formula 1.

3. A compound in accordance with claim 1 having the structure of formula 2.

4. A compound in accordance with claim 1 wherein X is —$C\equiv C$—.

5. A compound in accordance with claim 1 wherein Y is a bivalent phenyl, group.

6. A compound having the structure selected from formula (a) and formula (b)

formula (a)

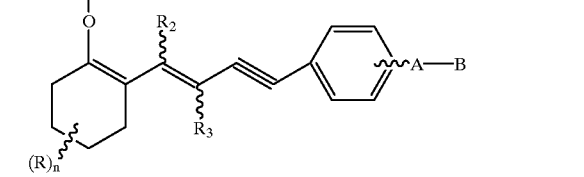

formula (b)

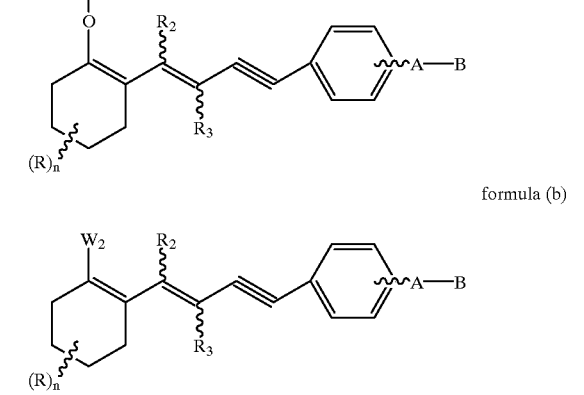

where $R_1$ is alkyl of 1 to 10 carbons, RCO, or $C_{1-C_6}$trialkylsilyl;

$W_2$ is $CH_2OR_2$, $R_2CO$, $CO_2R_2$, or $CON(R_2)_2$;

R is H, lower alkyl of 1 to 10 carbons, cycloalkyl of 3 to 10 carbons, halogen, $(C_{1-10}$-lower alkyl$)_3$-silyl, $C_{1-10}$-lower alkylphenyl, or phenyl-$C_{1-10}$-lower alkyl;

$R_2$ and $R_3$ independently are H, lower alkyl of 1 to 10 carbons cycloalkyl of 3 to 10 carbons, $(C_{1-10}$-lower alkyl$)3$-silyl, $C_{1-10}$-lower alkylphenyl, or phenyl-$C_{1-10}$-lower alkyl;

n is an integer having the values of 0 to 6;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical or 2–5 carbons, or a pharmaceutically acceptable salt of said compound.

7. A compound in accordance with claim 6 wherein R is methyl.

8. A compound in accordance with claim 6 wherein $R_2$ and $R_3$ are H.

9. A compound in accordance with claim 6 wherein n is 1 or 2.

10. A compound in accordance with claim 6 wherein the A-B group is $(CH_2)_q$—COOH or $(CH_2)_q$—COOR$_8$ where q is 0 or a pharmaceutically acceptable salt of said compound.

11. A compound in accordance with claim 10 wherein the A-B group is in the 4-position on the phenyl ring relative to the ethynyl group.

12. A compound of the formula

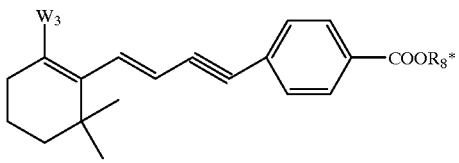

wherein $W_3$ is $R_1COO$, $C_1$–$C_6$ (trialkylsilyl)oxy, or $CO_2R_1$ where $R_1$ is alkyl, and
$R_8^*$ is H, alkyl, trialkylsilyl, (trialkylsilyl)alkyl, where alkyl is defined as lower alkyl having 1 to 6 carbons, cyclic or branch-chained alkyl of 3 to 6 carbons, or a pharmaceutically acceptable salt of said compound.

13. A compound in accordance with claim 12 where $W_3$ is $CH_3CO$.

14. A compound in accordance with claim 13 where $R_8^*$ is H or a pharmaceutically acceptable salt of said compound.

15. A compound in accordance with claim 13 where $R_8^*$ is ethyl.

16. A compound in accordance with claim 13 where $R_8^*$ is $(CH_3)_3SiCH_2CH_2$.

17. A compound in accordance with claim 12 where $W_3$ is $(CH_3)_3SiO$.

18. A compound in accordance with claim 17 where $R_8^*$ is H or a pharmaceutically acceptable salt of said compound.

19. A compound in accordance with claim 17 where $R8^*$ is ethyl.

20. A compound in accordance with claim 12 where $W_3$ is $CO_2CH_3$.

21. A compound in accordance with claim 20 where $R_8^*$ is H or a pharmaceutically acceptable salt of said compound.

22. A compound in accordance with claim 20 where $R_8^*$ is ethyl.

* * * * *